US012023117B2

(12) United States Patent
Klingbeil et al.

(10) Patent No.: US 12,023,117 B2
(45) Date of Patent: Jul. 2, 2024

(54) PROJECTION OF USER INTERFACE POSE COMMAND TO REDUCED DEGREE OF FREEDOM SPACE FOR A SURGICAL ROBOT

(71) Applicant: Verb Surgical Inc., Santa Clara, CA (US)

(72) Inventors: Ellen Klingbeil, Santa Clara, CA (US); Renbin Zhou, Santa Clara, CA (US); Haoran Yu, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 373 days.

(21) Appl. No.: 17/368,227

(22) Filed: Jul. 6, 2021

(65) Prior Publication Data

US 2023/0011725 A1 Jan. 12, 2023

(51) Int. Cl.
*A61B 34/35* (2016.01)
*A61B 34/00* (2016.01)
*A61B 34/30* (2016.01)

(52) U.S. Cl.
CPC .............. *A61B 34/35* (2016.02); *A61B 34/25* (2016.02); *A61B 34/74* (2016.02); *A61B 2034/305* (2016.02)

(58) Field of Classification Search
CPC ......... A61B 34/35; A61B 34/25; A61B 34/74; A61B 2034/305; A61B 2034/742; A61B 34/30; A61B 2017/00203; A61B 2017/00216
USPC ................. 700/245–264; 318/568.11–568.25
See application file for complete search history.

(56) References Cited

U.S. PATENT DOCUMENTS

| | | | |
|---|---|---|---|
| 10,052,164 B2 * | 8/2018 | Overmyer | A61B 34/74 |
| 11,648,681 B2 * | 5/2023 | Ju | B25J 9/1607 |
| | | | 700/245 |
| 2012/0176306 A1 | 7/2012 | Lightcap et al. | |
| 2014/0320489 A1 | 10/2014 | Chizeck et al. | |
| 2017/0020615 A1 | 1/2017 | Koenig | |
| 2017/0095295 A1 * | 4/2017 | Overmyer | B25J 13/02 |
| 2017/0333139 A1 * | 11/2017 | Suresh | A61B 34/30 |
| 2018/0049818 A1 * | 2/2018 | Yates | B25J 9/04 |
| 2019/0105117 A1 | 4/2019 | Brisson | |

(Continued)

FOREIGN PATENT DOCUMENTS

| | | | | |
|---|---|---|---|---|
| EP | 3838501 A1 * | 6/2021 | | B25J 9/0057 |
| KR | 20150127129 A | 11/2015 | | |
| WO | 2022046053 A1 | 3/2022 | | |

OTHER PUBLICATIONS

The International Search Report and Written Opinion of the International Searching Authority for International Application No. PCT/IB2022/055446 dated Sep. 19, 2022.

(Continued)

*Primary Examiner* — Jaime Figueroa

(74) *Attorney, Agent, or Firm* — Lempia Summerfield Katz LLC

(57) ABSTRACT

For teleoperation of a surgical robotic system, the user command for the pose of the end effector is projected into a subspace reachable by the end effector. For example, a user command with six DOF is projected to a five DOF subspace. The six DOF user interface device may be used to more intuitively control, based on the projection, the end effector with the limited DOF relative to the user interface device.

19 Claims, 4 Drawing Sheets

(56) References Cited

U.S. PATENT DOCUMENTS

| | | |
|---|---|---|
| 2019/0176334 A1 | 6/2019 | Zhou et al. |
| 2020/0030096 A1 * | 1/2020 | Zeitani |
| 2020/0055192 A1 * | 2/2020 | Ju .................... B25J 9/1602 |
| 2020/0352663 A1 | 11/2020 | Klingbeil et al. |
| 2021/0016445 A1 | 1/2021 | Zhou et al. |
| 2021/0121257 A1 | 4/2021 | Yu |

OTHER PUBLICATIONS

Kucuk, Serdar, and Zafer Bingul. Robot kinematics: Forward and inverse kinematics. Intech Open Access Publisher, 2006. pp. 117-148.

Moulton, Joshua, James Pellegrin, and Matthew Stephenson. "Planar Robots and the Inverse Kinematic Problem: an Application of Groebner Bases." pp. 1-12. Retrieved Jun. 30, 2021.

* cited by examiner

US 12,023,117 B2

PROJECTION OF USER INTERFACE POSE COMMAND TO REDUCED DEGREE OF FREEDOM SPACE FOR A SURGICAL ROBOT

BACKGROUND

The present embodiments relate to robotic systems for minimally-invasive surgery (MIS). MIS may be performed with robotic systems that include one or more robotic arms for manipulating surgical tools based on commands from a remote operator. A robotic arm may, for example, support at its distal end various surgical end effectors, including staplers, scalpels, imaging devices (e.g., endoscope), clamps, and scissors. Using the robotic system, the surgeon controls the robotic arms and end effectors in teleoperation during MIS.

Different end effectors, in combination with the robotic arms, have different numbers of degrees of freedom (DOF). For example, a stapler has five DOF in teleoperation. Five active joints, and corresponding DOF, includes two joints on the instrument (e.g., rotation and articulate to control yaw) and three joints on the robotic arm (e.g., spherical rotate, spherical pitch, and tool translate). The end effector is positioned and oriented with only five DOF. In yet another example, an endoscope or ultrasound scalpel has four DOF in teleoperation. Four active joints, and corresponding DOF, include one joint on the instrument (e.g., rotation) and three joints on the robotic arm (e.g., spherical rotate, spherical pitch, and tool translate).

During teleoperation, the user inputs using a user input device with a greater number of DOF, such as six DOF. These user pose commands in Cartesian space are translated into joints motions, such that the instrument follows the user commands or inputs with controlled accuracy. Tools having fewer DOFs than the input do not track the more arbitrary spatial commands (position and orientation) from the user input. This can lead to undesirable or un-intuitive behavior in the joint commands where the commanded motion is in a direction that is not feasible for the robot. Where the user input is ungrounded (e.g., 6 DOF), the motion of the user input device cannot be restricted by mechanical fixtures or haptic feedback to prevent the user from inputting motion for which the end effector is not capable.

SUMMARY

By way of introduction, the preferred embodiments described below include methods, systems, instructions, and computer readable media for teleoperation of a surgical robotic system. The user input for the pose of the end effector is projected into a subspace reachable by the end effector. For example, a user input with six DOF is projected to a five DOF subspace. The six DOF user interface device may be used to more intuitively control, based on the projection, the end effector with the limited DOF relative to the user interface device.

In a first aspect, a method is provided for teleoperation of a surgical robotic system. A user input to move a surgical tool coupled to a robotic arm is received. The user input has six degrees of freedom where the surgical tool has a lesser number of degrees of freedom. The user input is projected to the lesser number of degrees of freedom. Joint motion of the robotic arm and surgical tool is solved from the projected user input with inverse kinematics. The robotic arm and/or surgical tool are moved based on a solution from the solving.

In a second aspect, a method is provided for accounting for a limited degree of freedom of a tool in a surgical robotic system. A first pose from an ungrounded user interface with six degrees of freedom is projected to a second pose of an end effector of a surgical tool held by a robotic arm. The second pose has only four or five degrees of freedom. The end effector is controlled based on the second pose.

In a third aspect, a surgical robotic system is provided. A surgical instrument is mountable to a robotic arm. The surgical instrument has an end effector where rotation about one axis is coupled to rotation about another axis. A user interface device has three degrees of freedom in rotation. A controller is configured to project a user command from the user interface device for rotation about the one axis to rotations about the one axis and the other axis.

The present invention is defined by the following claims, and nothing in this section should be taken as a limitation on those claims. Any teaching for one type of claim (e.g., method) may be applicable to another type of claim (e.g., computer readable storage medium or system). Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A pose command from a user interface device is projected to a reduced DOF space. For example, 6D pose commands from an ungrounded user interface device are projected by a program into the reachable subspace during teleoperation. To achieve arbitrary end effector positions and orientations in 6D, the robot manipulator must have six actuated DOF or joints. Thus, for teleoperation with a surgical instrument having more limited DOF (e.g. a stapler instrument), the 6D pose commands are projected into a subspace for the more limited DOF (e.g., a 5D or 4D subspace) that is reachable by the robot end effector.

Different subspaces may be used for the projection. The DOF for the subspace may be any combination of translation and rotation (e.g., articulation and orientation) with the limited DOF, such as translation with 3 DOF and rotation with 2 DOF. There is more than one possible choice for the subspace (e.g., 4D or 5D subspace) onto which to project the 6D pose command. The choice of projection method may affect the user's ease of controlling the surgical instrument. The user is able to move the user interface device more freely in position and orientation (e.g., 6D), but the end effector will only move in the subspace according to the projection method. Thus, motion in one or more DOF direction is lost or limited, making it more difficult for the user to place the end effector position and orientation at a desired configuration. In one embodiment, the subspace has only 1 or 2 DOF of rotation and 3 DOF for translation to make the user interface as intuitive as possible. Other subspaces may be used.

Figure 1:
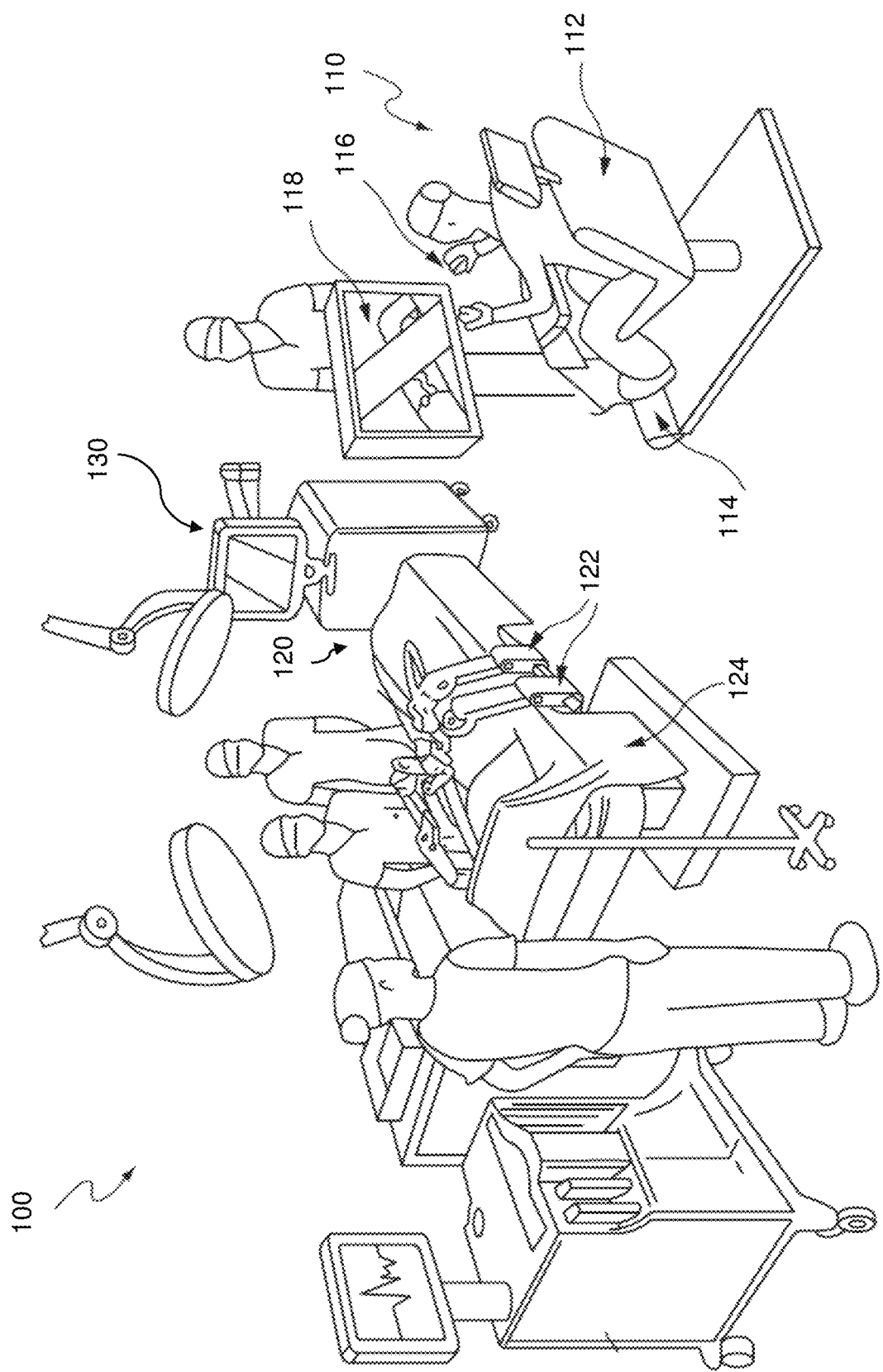
FIG. 1 is an illustration of one embodiment of an operating room environment with a surgical robotic system according to one embodiment.
Figure 2:
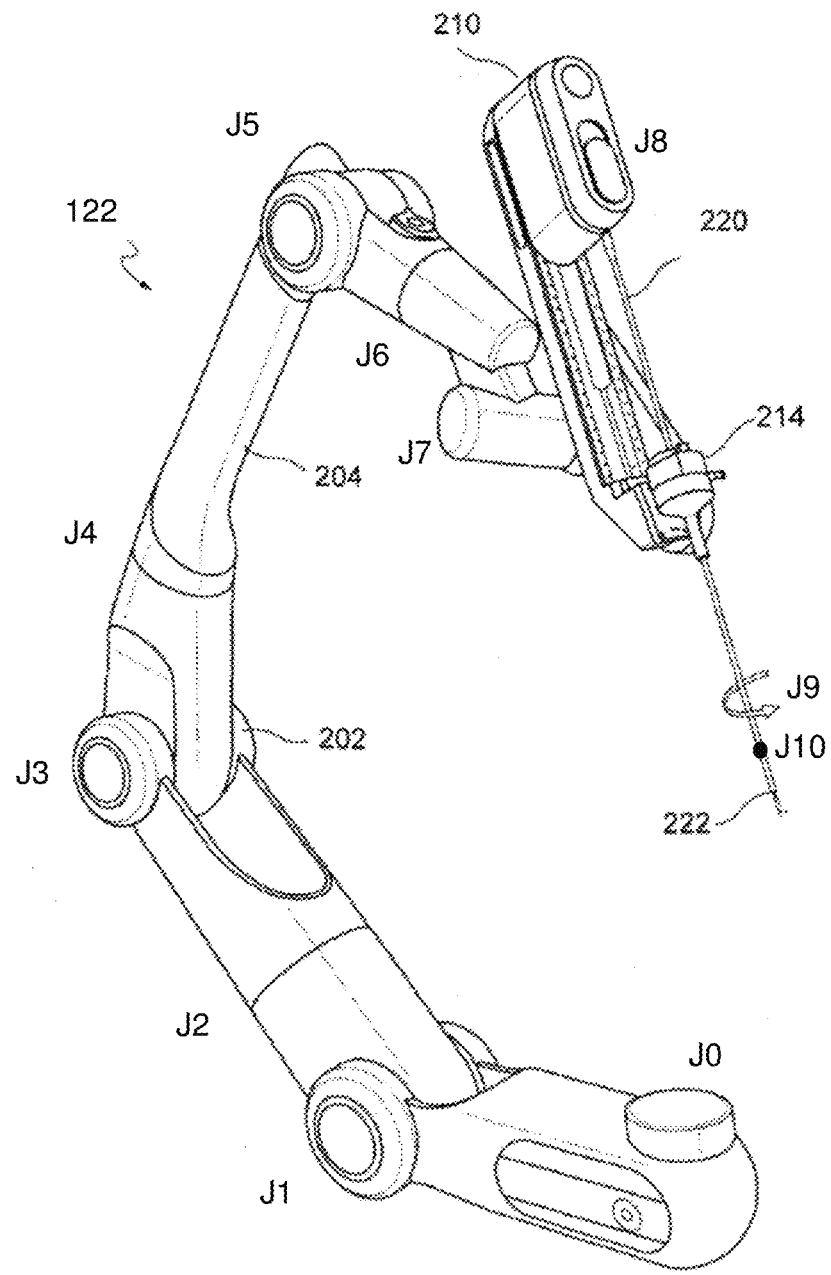
FIG. 2 illustrates an example surgical robot arm and surgical tool.

FIGS. 1 and 2 show an example surgical robotic system. The approaches for projection of the user inputs or commands for the end effector to a lower dimensional subspace are discussed below in reference to this example system. Other surgical robotic systems and surgical robots or non-surgical robotic systems and robots may use the projection to reduce dimensionality of the user command for pose or change in pose of the end effector.

Figure 3:
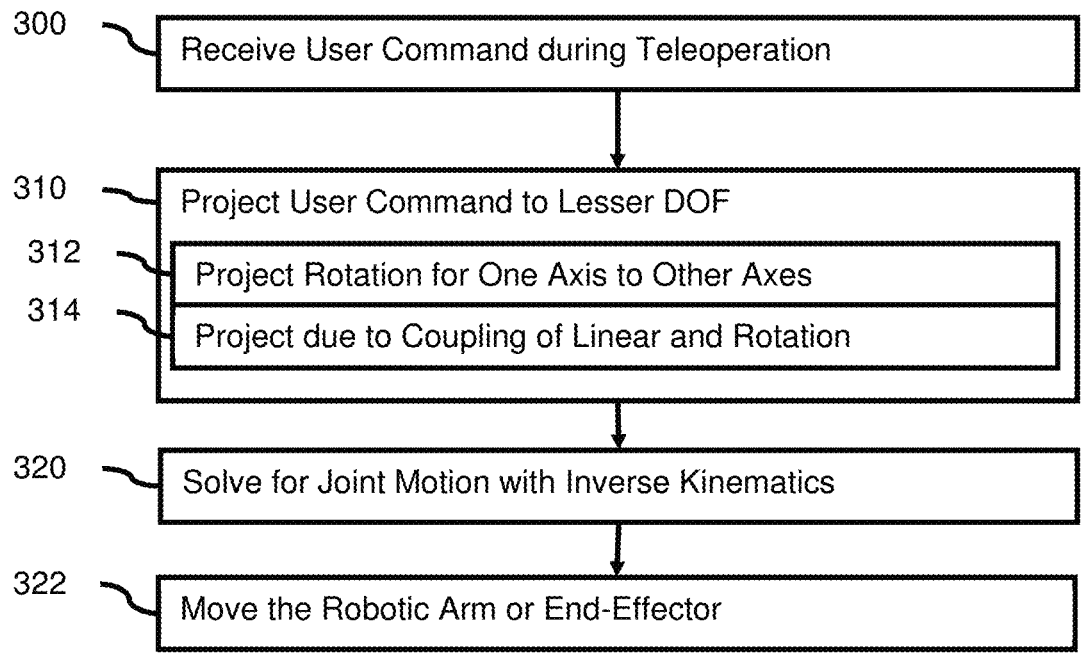
FIG. 3 is a flow chart diagram of one embodiment of a method for teleoperation of a surgical robotic system.
Figure 4:
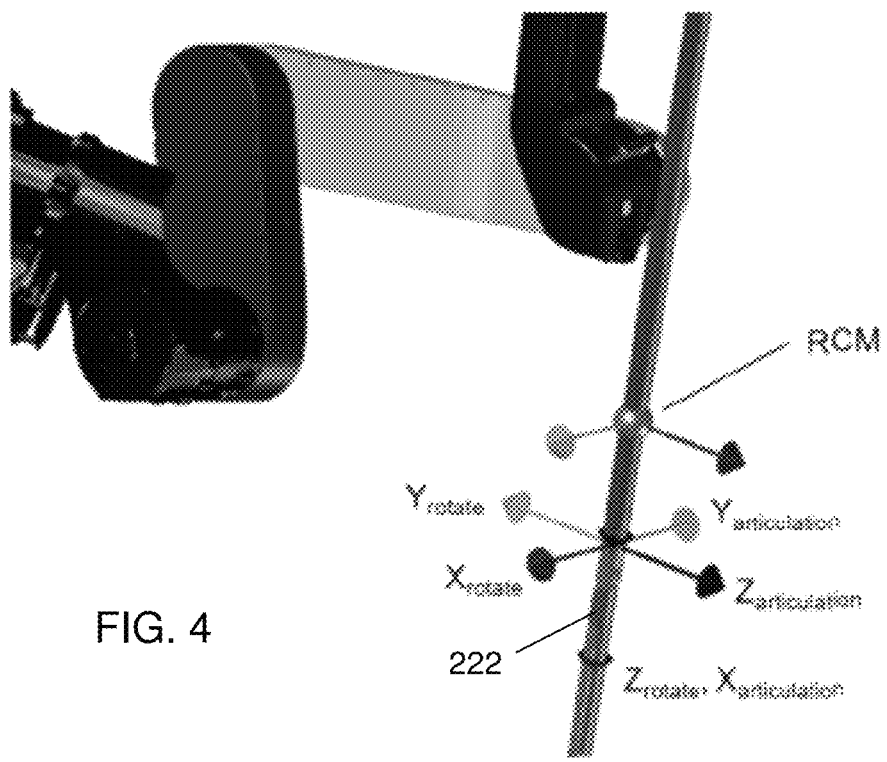
FIG. 4 shows some example frames of reference for a robotic arm and surgical tool.

FIGS. 3 and 4 are directed to projection of user inputs or commands in command space in teleoperation. FIG. 6 is directed to a system for using the projection to form a projected command, which is used in the inverse kinematics with a medical robotic system for teleoperation.

FIG. 1 is a diagram illustrating an example operating room environment with a surgical robotic system 100 for which commands from the user are converted into motion of the surgical robotic arms 122 with inverse kinematics. The surgical robotic system 100 includes a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. Additional, different, or fewer components may be provided, such as combining the control tower 130 with the console 110 or surgical robot 120. The robotic arms 122 are shown as table-mounted, but in other configurations, the robotic arms 122 may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may include a seat 112, pedals 114, one or more handheld user interface devices (UIDs) 116, and an open display 118 configured to display, for example, a view of the surgical site inside a patient and graphic user interface. As shown in the exemplary user console 110, a surgeon sitting in the seat 112 and viewing the open display 118 may manipulate the pedals 114 and/or handheld user interface devices 116 to remotely and directly control the robotic arms 122 and/or surgical instruments mounted to the distal ends of the arms 122. The user inputs commands for the movement of the surgical arms 122 and/or end effectors. This user control determines pose (position and orientation) of the robotic arms 122. The surgeon sitting in the seat 112 may view and interact with the display 118 to input commands for movement in teleoperation of the robotic arms 122 and/or surgical instruments in the surgery.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery using teleoperation. The movements may be surgeon, patient, and/or situation specific, so may vary. Manual assistance may also be provided at the procedure table by sterile-gowned personnel, who may perform tasks including but not limited to, retracting tissues or performing manual repositioning or tool exchange involving one or more robotic arms 122. Some surgical tasks, such as retracting, suturing, stapling, or other tissue manipulation, may instead be performed by one or more robotic arms 122 (e.g., third or fourth arms). Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or print-out, whether electronic or hard copy, such as via the user console 110.

In some aspects, the communication between the surgical robot 120 and the user console 110 may be through the control tower 130, which may translate user input commands from the user console 110 to robotic control commands and transmit the control commands to the surgical robot 120. The control tower 130 performs inverse kinematics. The control tower 130 may also transmit status and feedback from the robot 120 back to the user console 110. The connections between the surgical robot 120, the user console 110, and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform preoperative setup. During the preoperative setup, the main components of the surgical robotic system (e.g., table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms 122 from their stowed position for sterile draping. After draping, the arms 122 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 122 over the patient and attach each arm 122 to a corresponding sleeve. The surgical robotic system 100 has the capability to uniquely identify each tool (endoscope and surgical instruments) upon attachment and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery as teleoperation using the tools controlled by two master UIDs 116 and foot pedals 114. The system translates the surgeon's hand, wrist, and finger movements through the master UIDs 116 into precise real-time movements of the surgical tools. Therefore in direct teleoperation, the system constantly monitors every surgical maneuver of the surgeon and pauses instrument movement if the system is unable to precisely mirror the surgeon's hand motions. The UIDs 116 may move in six DOF, such as allowing translation in three dimensions and rotation about the three dimensions. The foot pedals 114 may be used to activate various system modes, such as endoscope control and various instrument functions including monopolar and bipolar cautery, without involving surgeon's hands removed from the master UIDs 116.

FIG. 2 is a schematic diagram illustrating one exemplary design of a robotic arm, a tool drive, and a cannula loaded with a robotic surgical tool, in accordance with aspects of the subject technology. As shown in FIG. 2, the example surgical robotic arm 122 may include a plurality of links (e.g., a link 204) and a plurality of actuated joint modules (e.g., a joint 202, see also joints J1-8) for actuating the plurality of links relative to one another. The joint modules may include various types, such as a pitch joint or a roll joint, which may substantially constrain the movement of the adjacent links around certain axes relative to others.

Also shown in the exemplary design of FIG. 2 is a tool drive 210 attached to the distal end of the robotic arm 122. The tool drive 210 may include a cannula 214 coupled to its end to receive and guide a surgical instrument 220 (e.g., endoscopes, staplers, scalpel, scissors, clamp, retractor, etc.). The surgical instrument (or "tool") 220 may include an end effector 222 at the distal end of the tool. The plurality of the joint modules of the robotic arm 122 can be actuated to position and orient the tool drive 210, which actuates the end effector 222 for robotic surgeries. The end effector 222 is at a tool shaft end and/or last joint (e.g., articulation joint J10). In other embodiments, the tool shaft end is a tip of a needle or other object.

In the example of FIG. 2, the joint J0 is a table pivot joint and resides under the surgical table top. Joint J0 is nominally held in place during surgery and may be used as a reference frame or base frame for operation of the robotic arm 122. Joints J1 to J5 form a setup or Cartesian arm and are nominally held in place during surgery or teleoperation, so do not contribute to motion during surgical teleoperation. Joints J6 and J7 form a spherical arm that may actively move during surgery or teleoperation. Joint J8 translates the tool 220, such as the end effector 222, as part of a tool driver. Joint J8 may actively move during surgery. Joint J9 rotates the longitudinal shaft of the tool 220 about the longitudinal axis. Joint J10 is a wrist on the tool 220, such as a wrist that rotates about one axis perpendicular to the longitudinal shaft.

Joints J6-10 actively position a tool shaft end (i.e., end effector 222) during surgery while maintaining an entry point into the patient at a fixed or stable location (i.e., remote center of motion) to avoid stress on the skin of the patient. During set-up, any of the joints J0-J10 may move. During surgery, the joints J6-10 may move subject to hardware or safety limitations on position, velocity, acceleration, and/or torque. The surgical tool 220 may include none, one, or more (e.g., three) joints, such as a joint for tool rotation plus any number of additional joints (e.g., wrists, rotation about a longitudinal axis, or other type of motion). Any number of degrees of freedom may be provided, such as the three degrees from the joints J6-8 and none, one, or more degrees from the surgical tool 220.

In the example of FIG. 2, the surgical tool includes joints J9 and J10, providing two DOF. In combination with the joints J6-8 in teleoperation, 5 DOF is provided. In other embodiments, 4 DOF is provided, such as with an endoscope without the articulation joint J10. Unlike instruments with fully articulated wrists, the example of FIG. 2 (e.g., a stapling instrument) may only have a single wrist joint J10. Thus, during teleoperation, only five active joints (e.g., three arm joints J6-8 plus the instrument shaft roll joint J9 and the wrist articulation joint J10) are available to position and orient the wrist and end effector 222.

In the example of FIG. 1, the UID 116 is ungrounded. The UID 116 does not physically and/or directly connect to a base but is instead free to move in 6 DOF in a Cartesian or other user command sensor space. The UID 116 is ungrounded. The term "ungrounded" is intended to refer to implementations where, for example, both UIDs are neither mechanically nor kinematically constrained with respect to the user console. The UID 116 does not include a structure that limits movement and/or structure for directional haptic feedback. A wire may or may not flexibly connect to the UID 116. Given that, in general, a robot manipulator with five actuated joints J6-10 for teleoperation cannot achieve arbitrary positions in 6D, 6D pose or commands from the UID 116 are projected into a 4D or 5D subspace, which is reachable by the robot end effector 222.

FIG. 3 is a flow chart diagram of one embodiment of a method for teleoperation of a surgical robotic system. The method accounts for any limited DOF of a tool or surgical instrument. Projection of the user input or command to a subspace for the surgical instrument 220 provides a projected command to be used to solve for robotic control or movement of a robotic arm 122 and surgical tool 220. To address the limited DOF of the tool 220, projection is performed to convert the command to control in the limited DOF.

The method of FIG. 3 is implemented by a control processor, such as the control tower 130, computer, workstation, sever, or another processor performing act 310. Any computer of the surgical robotic system 100 may be used. A user interface provides the movement commands from the user received in act 300. The robotic arm 122 and/or surgical tool 220 are moved using the instructions or control from the control processor in act 320. Other devices may perform and/or be used in any of the acts.

The acts are performed in the order shown or other orders. The various acts 312 and 314 that are part of the solving of act 310 may be performed in any order and/or simultaneously.

Additional, different, or fewer acts may be used. For example, act 322 is not provided. As another example, the movement commands are from a programmed or processor determined sequence (e.g., operation template), so act 300 is not provided. In another example, acts for initially positioning the surgical tool 220 in the patient, planning surgery, and/or removing the surgical tool 220 from the patient may be provided.

In act 300, the control processor receives a user input command to move the surgical tool 220 through movement of the robotic arm 122 and/or surgical tool 220 of the robotic arm 122 during the teleoperation. The user input is received by the control processor from the user console 110, such as the UIDs 116, via wireless or wired interface. In other embodiments, the user inputs are received by loading from memory or transmission over a computer network.

In preparation for teleoperation, the user sits down at the surgeon console 110. After positioning of the robot arm 122 for teleoperation, one or more joints are locked in place with a fixed remote center of motion (RCM) at the patient skin or incision entry point. For example, joints J0-J5 (see FIG. 2) are locked. The locking is by a brake and/or avoiding energizing the motors for the joints. These joints remain locked during teleoperation.

During teleoperation, the user enters commands to move the end effector 222 of the surgical instrument 220. The commands are for motion of the end effector 222. Different commands may be provided for different movements. The commands may be for movement of other parts of the surgical instrument 220. A change in pose of the end effector 222 may be entered by sensing a pose or position and orientation or by sensing the change. These commands may not be for movement of particular joints. The control processor is to convert the movement commands of the end effector 222 or user input to controls of particular joints of the robotic arm 122 and/or surgical tool 220.

In one embodiment, user motion is tracked using a sensor. For example, the user holds a device, such as a pen or the UID 116. A magnetic position sensor and/or inertial measurement unit may be used to determine pose and/or change in pose of the pen or UID 116. As another example, the user holds a marker with a structure allowing for visual tracking, such as optical patterns or structures on one or more parts of the marker. A stereo camera and/or depth camera tracks the motion of the marker. Other user input devices may be used.

The user inputs are in 6 DOF. Translation along and rotation about all of three orthogonal axes is provided. The user inputs may be for control of a surgical instrument 220 or end effector with fewer than six DOF, such as four or five DOF (e.g., translation along three axes but rotation along one or two axes). Alternatively, the user inputs are in less than 6 DOF but more DOF than provided by the robotic arm 122 and surgical instrument 220.

The user inputs with six DOF may be for controlling movement for fewer than six DOF. Five, four, or fewer active joints may be provided. FIG. 2 shows the robotic arm 122 and the surgical tool 220 providing five DOF, such as where the surgical tool 220 is a stapler. The active joints include three joints on the robotic arm 122—spherical rotation joint J6, spherical pitch joint J7, and tool translation joint J8. The active joints include two joints on the surgical tool 220—rotation at joint J9 and articulation joint J10 as a wrist. In an example of four DOF, the active joints include three joints on the robotic arm 122—spherical rotation joint J6, spherical pitch joint J7, and tool translation joint J8—and one active joint on the surgical tool—rotation at joint J9. Other active joint arrangements may be used, such as providing two or fewer DOF on the robotic arm during teleoperation.

The DOF of the user inputs or commands is greater than the DOF of movement of the end effector 222. For example, the tool 220 has a limited degree of freedom, such as four or five DOF in combination of the tool 220 with the robotic arm 122 during teleoperation. The user inputs and corresponding UIDs 116 have six DOF. This may result in receiving user inputs with rotation and/or translation of the tool about or along an axis where the tool is not rotatable about or translatable along that axis when all other joints are stationary. In the example of FIG. 2, the tool may be rotatable only about two axes by rotation joint J9 and wrist articulation joint J10, yet the user inputs may include rotation of the end effector 222 about all or any of three axes.

The end effector 222 may be moveable in six DOF using a combination of joints but cannot move in at least one DOF where the command is to move only in that DOF. During teleoperation, the remote center of motion (RCM) is a point on the vector pointing along the instrument shaft towards the end-effector 222 that is constrained to remain stationary. This is achieved through the manipulator mechanical design (via the spherical pitch joint design) or by control of the joints. The RCM constraint is satisfied independently of the command for the spherical arm joints (J6-J10) to move the end effector 222 during teleoperation.

In one embodiment, the end effector 222 is treated as being at the articulation joint J10. The frame of reference for the end effector is coincident with the articulation joint frame. FIG. 4 shows these frames of reference along the tool 220, including the RCM frame of reference where the RCM is to remain stationary along a plane tangential to the skin of the patient at the access point into the patient. The rotation and translation of the end effector 222 are represented as a tool rotate joint frame and an articulation joint frame. The rotate joint frame includes X, Y, and Z rotation axes, and the articulation joint frame includes X, Y, and Z articulation axes. The end effector frame for teleoperation is specified to be coincident with the articulation frame, which is aligned with the rotation joint frame (e.g., Y rotate is along but an inverse of Z articulation, X rotate is along but an inverse of Y articulation, and Z rotate is along and not an inverse of X articulation). Other arrangements or frames of reference may be used.

In act 310, the control processor projects the user input to a lesser number of degrees of freedom than the six degrees of freedom of the UID 116. The user inputs a pose or change in pose using the UID 116. This user input for control of the end effector 222 has six DOF, so the pose or change in pose with 6 DOF is converted to a pose or change in pose for which the surgical tool is capable, such as pose or change with 5 DOF.

In one embodiment, the 6D pose command for the end effector 222 at a given time is provided. The pose for the current time may be computed from the pose from or for the end effector pose command at the previous time step and the motion of the UID 116 between the previous and current time step. Alternatively, the 6D pose command for the current time is based on a current pose of the UID 116 or a measure of the change without reference to an earlier pose.

Given that the UID 116 is ungrounded, the limitations on the robot actuation may render it infeasible for the robot end effector 222 to achieve the motion of the human hand within or pose for a given time step. For example, rotation about one axis with no rotation about any other axis may not be possible. The projection converts the user pose command into realizable motion or pose. A pose command for the end effector 222 is available that, after projection, is generally achievable by the robotic arm 122 and surgical instrument 220.

In one embodiment, the projection is from the pose with 6 DOF to a pose with only 4 or 5 DOF. Rotation, translation, or both rotation and translation may be limited. In the example used herein (see FIG. 2), the projection is from 6 DOF to 5 DOF where rotation about one axis alone is not available. The projection is from 3 DOF of rotation to 2 DOF of rotation while the 3 DOF for translation is maintained or not altered in the projection. In alternative embodiments, it may be translation along one axis alone not being available. For example, a change in position command with 3 DOF is projected onto a 2D subspace, and the full orientation command (e.g., 3 DOF) is maintained or unaltered. The delta position command is projected onto the X rotate and Z rotate axes. This would result in the user being unable to instantaneously produce linear motion along the Y rotate axis, however, the user would have full orientation control. Other axes may be used. In the embodiment for projection of 6 DOF to 5 DOF where the missing DOF is rotation about one axis, the 3 DOF for translation are maintained and the 3 DOF of rotation are projected to 2 DOF. The rotation about the missing DOF is projected onto the rotations about the remaining axes.

In one approach, the command end effector orientation are represented as a rotation matrix. Other representations may be used. The position and rotation are defined with respect to a base frame at a given time t. Other frames of reference may be used. The position is denoted as $p_{ee\text{-}base}(t) \in R^{3 \times 1}$, and the rotation is denoted as $R_{ee}^{base}(t) \in R^{3 \times 3}$, where ee designates the end effector and base designates the base frame of reference. The orientation of the tool rotate joint frame (see FIG. 4) with respect to the base frame at time t is denoted as $R_{rotate}^{base}(t)$, where rotate designates the tool rotate joint frame. Other definitions and/or frames of reference may be used.

The projection is from 6 DOF to 5 DOF or 3 DOF for rotation (or translation) to 2 DOF for rotation (or translation. The translation or rotation in 3 DOF is maintained or not changed in the projection.

In one embodiment, given the kinematics of the spherical arm of the robotic arm 122 of FIGS. 2 and 4, it is not possible for the end effector 222 to instantaneously rotate about the Y articulation or X rotation axis while maintaining a fixed position and fixed orientation in the remaining axes. To handle this, the change in end effector command (delta end effector command) from the previous time step to the current time step is projected onto a 5D subspace. The delta end effector orientation command is projected onto the Z rotate axis, which is aligned with the tool rotation joint axis, and Z articulation axis or inverse to the Y rotate axis, which is aligned with the wrist articulation joint axis. The surgical instrument 220 is able to produce rotations instantaneously about these Y and Z rotate axes. The delta in rotation between the end effector orientation command at time t+1 and time t represented in end effector coordinates is given by:

$$\Delta R_{ee(t+1)}^{ee(t)} = (R_{ee}^{base}(t))^T * R_{ee}^{base}(t+1)$$

where T is the transpose. The change in rotation about three axes in an end effector frame of reference (e.g., at the articulation joint J10) is provided by the rotation matrices at different times.

The rotation of the user input for rotation of the end effector 222 is projected from rotation about three axes to rotation about two of the axes. Any projection function, such as a linear or non-linear mapping, may be used. In one embodiment, the rotation is removed. In other embodiments, the projection is converted with more than mere removal. For example, the projection uses a function relating rotation about one axis with rotation about one or more other axes. A dot product of rotation about the axis to be removed with a change in rotation of the end effector is multiplied by the rotation about the axis to be removed. The result is subtracted from the rotation matrix for the user input.

In one embodiment, the projection uses conversion from the rotation matrix to an axis-angle representation. The rotation matrix representation is converted to an axis-angle representation. The projection is performed using the axis-angle representation. A result of the projection is converted back to the rotation matrix representation. For this approach, the delta end effector orientation is converted into the axis-angle representation $\Delta \theta_{ee(t+1)}^{ee(t)} \in R^{3 \times 1}$. This axis-angle representation is projected onto the Y and Z axes of the tool rotate joint frame. For example, the following equation is used:

$$(\Delta \theta_{ee(t+1)}^{ee(t)})_{projected} = \Delta \theta_{ee(t+1)}^{ee(t)} - (\Delta \theta_{ee(t+1)}^{ee(t)} \cdot X_{rotate\text{-}in\text{-}ee}(t)) * X_{rotate\text{-}in\text{-}ee}(t)$$

where (·) is the dot product operator. $X_{rotate\text{-}in\text{-}ee}$ is the X axis of the tool rotate frame expressed in end effector frame coordinates and is computed using the following equation:

$$R_{rotate}^{ee}(t) = [X_{rotate\text{-}in\text{-}ee} Y_{rotate\text{-}in\text{-}ee} Z_{rotate\text{-}in\text{-}ee}] = (R_{ee}^{base}(t))^T * R_{rotate}^{base}(t)$$

The projected axis-angle representation $(\Delta \theta_{ee(t+1)}^{ee(t)})_{projected}$ is converted back into rotation matrix representation as $(\Delta R_{ee(t+1)}^{ee(t)})_{projected}$. Other conversions or representations or calculation in the rotation matrix may be used.

The projection to the reduced dimension subspace may be used alone. In other embodiments, the projection includes consideration for other physical relationships of the robotic arm 122 and surgical instrument 220. In one embodiment, the projection includes projection to the reduced dimension subspace (e.g., 6 DOF to 5 DOF) of the end effector command as well as a projection of a change in rotation due to coupling between translation and rotation. In movement of the end effector 222, the translation and rotation provided by the robotic arm 122 and surgical instrument 220 are coupled. The rotation and translation about one axis (e.g., the rotation axis being removed by projection) may be coupled so that translation along the axis affects rotation. The rotation and translation along other axes and/or between axes may be coupled. The projection may include consideration of one or more of these relationships.

The remote center of motion limitation on movement of the end effector 222 impacts or causes the coupling. The projection may include a similarity transform to account for the remote-center-of-motion of the robotic arm 122 with coupling of translation and rotation.

In one embodiment, the projection to the reduced dimension subspace nulls out orientation or change in orientation along the $X_{rotate}$ axis. The change in position is unchanged by the projection. In order to achieve a desired delta in commanded end effector position along the $Y_{rotate}$ direction, a delta in orientation occurs about the $X_{rotate}$ axis as these motions are coupled and cannot be controlled independently. This delta in orientation is computed given the constraint that the RCM position is fixed.

The orientation and position of the RCM frame with respect to the base frame are denoted as $p_{rcm\text{-}base}(t)$ and $R_{rcm}^{base}(t)$, respectively. The commanded end effector poses with respect to the RCM frame at times t and t+1 and the orientation of the end effector frame with respect to the RCM frame at time t are computed as:

$$p_{rcm\text{-}ee}(t) = (R_{rcm}^{base}(t))^{T} * (p_{ee\text{-}base}(t) - p_{rcm\text{-}base}(t))$$

$$p_{rcm\text{-}ee}(t+1) = (R_{rcm}^{base}(t))^{T} * (p_{ee\text{-}base}(t+1) - p_{rcm\text{-}base}(t))$$

$$R_{ee}^{rcm}(t) = (R_{rcm}^{base}(t))^{T} R_{ee}^{base}(t)$$

The rotation or change in rotation for time t+1 is determined as part of the projection operation. The normalized unit vectors corresponding to $p_{rcm\text{-}ee}(t)$ and $p_{rcm\text{-}ee}(t+1)$ are denoted as $\hat{v}_{rcm\text{-}ee}(t)$ and $\hat{v}_{rcm\text{-}ee}(t+1)$, respectively. The rotation to transform the vector $\hat{v}_{rcm\text{-}ee}(t)$ into $\hat{v}_{rcm\text{-}ee}(t+1)$ is computed using Rodrigues' rotation formula. This rotation, in matrix representation, from the translation is denoted as $\Delta R_{ee\text{-}rcm\text{-}constraint}$. This rotation is converted into the end effector frame using the similarity transform, as represented by:

$$\Delta R_{ee\text{-}constraint(t+1)}^{ee\text{-}constraint(t)} = (R_{ee}^{rcm}(t))^{T} * \Delta R_{ee\text{-}rcm\text{-}constraint} * R_{ee}^{rcm}(t)$$

The result is a constrained rotation in the end effector frame. The axis angle representation of this rotation, denoted as $\Delta \theta_{ee\text{-}constraint(t+1)}^{ee\text{-}constraint}(t)$, is projected onto the $X_{rotate}$ axis as follows:

$$(\Delta \theta_{ee\text{-}constraint(t+1)}^{ee\text{-}constraint(t)})_{projected} = (\Delta \theta_{ee\text{-}constraint(t+1)}^{ee\text{-}constraint(t)} \cdot X_{rotate\_in\_ee}(t)) * X_{rotate\text{-}in\text{-}ee}(t)$$

This rotation is converted to the rotation matrix representation, denoted as $(\Delta R_{ee\text{-}constraint(t+1)}^{ee\text{-}constraint(t)}(t))_{projected}$. Other functions may be used to determine the rotation or change in rotation due to coupling or other physical constraint in movement of the robotic arm 122 and surgical instrument 220.

This projected change in rotation due to coupling is combined with the projection to reduce the DOF. Any combination may be used, such as a weighting, summation, or multiplication. The final projected user input is a function of both the change in rotation due to the coupling and the projection to the lesser number of DOF. In one embodiment, the function is a multiplication of the change in rotation due to the coupling, the projection to the lesser number, and the rotation about the three axes of the original user input for motion of the end effector. To produce the final projected end effector orientation command (e.g., change in orientation), the delta rotation command for DOF reduction and delta rotation due to the coupling between the linear motion and rotation about the $X_{rotate}$ axis are combined as follows:

$$(\Delta R_{ee}^{base}(t+1))_{projected} = R_{33}^{base}(t) * (\Delta R_{ee\text{-}constraint(t+1)}^{ee\text{-}constraint(t)})_{projected} * (\Delta R_{ee(t+1)}^{ee(t)})_{projected}$$

Other combinations may be used to determine the change in rotation from projection. The result is the user input for end effector pose or change in pose projected to the lower dimensional subspace to account for limitations of the rotation. The result is a projected user input for end effector pose or change in pose. The projection may be of the rotation of the pose while the translation is used without change.

It is assumed that the delta rotations are small given a real time teleoperation scenario due to frequent sampling or measurement of the user interface device 116. If the delta rotation is large, combining these delta rotations from dimensionality reduction and coupling may use an additional transformation to transform the delta rotation from coupling to be with respect to the frame produced by applying the delta rotation for dimensionality reduction. Without the additional transformation, both delta rotations are defined with respect to the end effector frame at time t.

The resulting projected user input or command is used for controlling the end effector 222 instead of the user input before projection. The end effector 222 is to be controlled based on the pose provided after projection.

In act 320, the control processor solves for joint motion of the robotic arm 122 and surgical tool 220 from the projected user command. The command, as projected rather than without projection, for motion or pose of the end effector is used to determine which joints to move, by how much, and in which direction. The receipt of the user input and the projection occur in a command space or the domain of the user input for control of the end effector 222. The projection is performed prior to solving for the joint motions. The solution then solves for the joint motions from the projected user command (e.g., the projected end effector pose or change in pose). The control processor solves by converting from the command space for the end effector 222 to a joint space for joints of the surgical tool 220 and robotic arm 122. The control processor translates the movement commands from the user to movement of the joints.

The controller or another processor solves for joint motion from the projected user command with inverse kinematics. The control processor solves for motion by the robotic arm 122 and/or the surgical tool 220 of the robotic arm 122 with an iterative solution. An iterative inverse kinematic solution is found. The control process may be input of the user inputs, iterative solution using inverse kinematics with a given termination check for the iterations, and output of a final result of joint commands. The inverse kinematics may incorporate limits on position, velocity, torque, and/or acceleration on the motion of the end effector and/or joints. The inverse kinematics is an optimization function, such as a minimization. For example, a difference between the projected change in pose and a change in pose resulting from joint positions of the surgical robotic system is minimized in act 312. The minimization provides for the change in the joint position given the change in pose. Other optimizations may be used.

In one embodiment, the inverse kinematics is performed as a least square minimization. Other minimizations may be used. The minimization is solved from in a control frame different than the end effector coordinate system. For example, the control frame is a frame of reference for the robotic arm 122, such as a coordinate system based on the joint J0 or a base of the robotic arm 122.

In act 322, the control processor causes movement of the robotic arm 122 and/or the surgical tool 220. The output movement commands for the active joints (e.g., joints J6-10 of FIG. 2) during teleoperation cause the joints to change position at the velocity and/or acceleration. The results from the inverse kinematics control the movement of the joints. The joint motion avoids rotation of the surgical tool 220 in ways that are not feasible. The solution from the inverse kinematics is used to move the surgical tool 220 by operation of joints of the surgical tool 220 and/or joints of the robotic arm 122 holding the surgical tool 220. The solved for changes in joint position control the surgical robotic system.

The expected behavior of the robotic arm 122 and surgical instrument 220 given the projection is that the robot end effector 222 will track the position command from the user input device 116, but the orientation command is projected onto a plane (i.e., from X, Y, Z (3D) to Y, Z (2D)). For example, if at a given time, the delta in orientation of the user interface device 116 and corresponding user input is about the $X_{rotate}$ axis and the user interface device 116 position is stationary, the end effector would remain stationary as the delta orientation command is projected into the plane that is orthogonal to $X_{rotate}$. With only rotation in X, the rotation does not occur due to the projection to a plane without an X rotation component. The user is not able to instantaneously produce an end effector rotation about the $X_{rotate}$ axis although the ungrounded user interface device 116 is free to rotate about that axis. The projection results a change in the mapping between the physical axes of the user interface device 116 and the end effector orientations. If the failure to rotate in this situation is undesirable to users, the user may be trained to learn to rotate the user interface device 116 predominantly in the projected subspace (e.g., rotation in Y and Z). Additionally or alternatively, the end effector orientation command may be used to attempt to keep the user interface device axes and end effector axes aligned.

Figure 5:
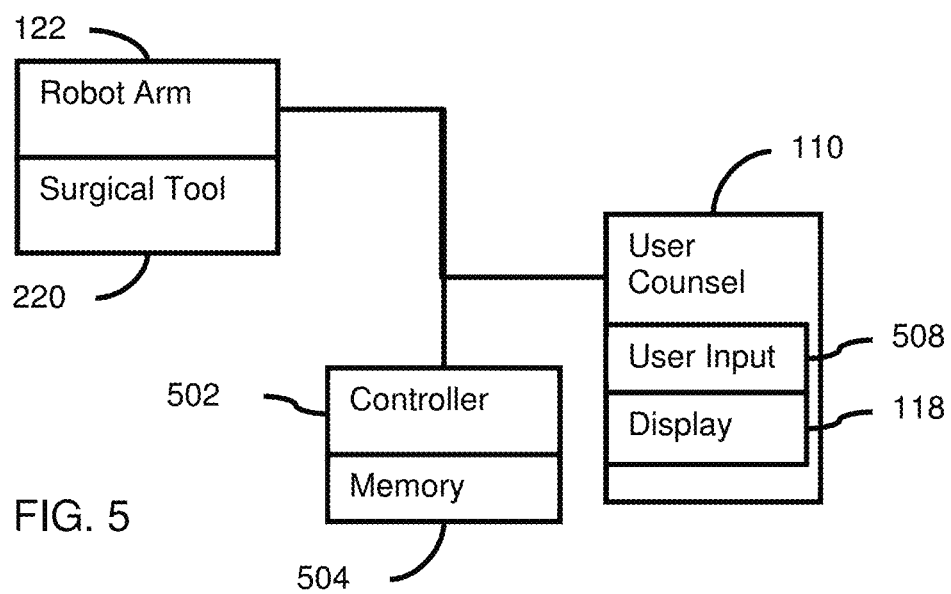
FIG. 5 is a block diagram of one embodiment of a surgical robotic system.

FIG. 5 shows a block diagram of one embodiment of a surgical robotic system for medical teleoperation. The user inputs from the user input 508 are projected to a lower dimensionality subspace. The robotic system is controlled based on the user command as projected. The system performs the method of FIG. 3 or another method.

The surgical robotic system includes one or more robot arms 122 with corresponding surgical instruments 220 or other types of instruments connected with the robot arms 122, a controller 502, and a memory 504. The user console 110 is represented or included as part of the surgical robot system but may be positioned remotely from or locally to the robot arm 122. Additional, different, or fewer components may be provided. For example, the robot arm 122, surgical instrument 220, and/or user console 110 are not provided.

The robotic arms 122 each include one or more links and joints. The joints may be pitch or roll joints. A tool drive and cannula for receiving and guiding a surgical tool may be provided on each of the robotic arms 122. Different combinations of links and joints may define or form different parts of the robotic arms 122, such as different parts having different degrees or types of movement (e.g., translation and/or rotation). Any now known or later develop robotic arm 122 with motors, sensors, links, joints, controllers, surgical instruments, and/or other structure may be used.

One or more robotic arms are provided. For example, three or four robotic arms 122 are provided. The robotic arms 122 mount to a table, such as a base of an operating table. Alternatively, cart, floor, ceiling, or other mounts may be used. The robotic arms 122 include a cable or wireless transceiver for communication with the processor 206 or an intermediary (e.g., control tower 130).

The robotic surgical instruments 220 are one or more graspers, retractors, scalpels, endoscopes, staplers, scissors, or other surgical device for manipulating tissue of the patient. The tissue manipulation may be direct, such as cutting or grasping. The tissue manipulation may be indirect, such as an endoscope pressing or contacting tissue as guided to image or view an interior portion of the patient. Different or the same type of instruments 220 may be mounted to different ones of the robot arms 122. For example, two robot arms 122 may have graspers, a third robot arm 122 may have a scalpel, and a fourth robot arm 122 may have an endoscope.

The robotic surgical instruments 220 connect to the distal ends of the robot arms 122 but may connect at other locations. The connection provides a drive so that the tool may be operated, such as closing a grasper or scissors and for operating joints of the surgical instrument 220.

One or more of the robotic surgical instruments 220 has limited motion. The surgical instrument 220 in combination with the robot arm 122 may have fewer than six DOF, such as having four or five DOF. For example, the robot arm 122 provides three joints while the surgical instrument 220 is limited to rotation about one axis or two axes. An endoscope as the surgical tool 220 may provide for just rotation about the long axis of the instrument 220 without rotation about two other orthogonal axes. A stapler as the surgical tool 220 may provide for rotation about the long axis and rotation about another axis for one joint without providing for rotation about a third axis. The robot arm 122 may allow for full 6 DOF. The robot arm 122 may have some movement locked during teleoperation. As a result, the surgical instrument 220 or the surgical instrument 220 in combination with the robot arm 122 may not be able to rotate and/or translate just about one or more axes. For example, the end effector 222 of the surgical instrument 220 as connected to the robotic arm 122 cannot rotate about one axis while not rotating about two other axes.

The user console 110 is a graphics user interface for interaction of the surgeon with the surgical robot system, such as with a processor (e.g., controller 502 or another controller) for controlling the robotic arms 122. The user interface includes a user input 508 and a display 118. The user input 508 and/or the display 118 are provided at the user console 110 and/or control tower 130 but may be at other locations.

The user input 508 is a button, a keyboard, a rocker, a joy stick, a trackball, a voice recognition circuit, a mouse, a touch pad, a touch screen, sliders, switches, UID 116, foot pedal 114, combinations thereof, or any other input device for inputting to the surgical robot. The user input 508 may be a sensor or sensors for detecting eye movement and/or blinking. In yet other embodiments, the user input 508 is a microphone for voice-based input. The user input 508 has a greater degree of freedom of motion than the end effector 222. For example, the UID 116 is untethered or ungrounded, so has 6 DOF. The end effector 222 may be limited to not rotate or translate about one or more axes where no motion is provided for other axes.

The display 118 is a monitor, liquid crystal display (LCD), projector, plasma display, CRT, printer, or other now known or later developed device for outputting visual information. In an alternative embodiment, the display 118 is a head mounted display. A speaker for output of audio information may be provided instead of or in addition to the display 118.

The controller 502 is a controller that drives and/or models the robotic arms 122 and/or surgical instruments 220. The controller 502 is a general processor, central processing unit, control processor, graphics processor, graphics processing unit, digital signal processor, application specific integrated circuit, field programmable gate array, digital circuit, analog circuit, artificial intelligence processor, combinations thereof, or other now known or later developed device for translating user inputs to joint commands for the robot arm 122 and/or surgical instrument 220. The controller 502 is a single device or multiple devices operating in serial, parallel, or separately. The controller 502 may be a main processor of a computer, such as a laptop, server, workstation, or desktop computer, or may be a processor for handling some tasks in a larger system. Based on hardware, software, firmware, or combinations thereof, the controller 502 is configured to implement instructions or perform acts.

The controller 502 is configured to project a user input from the user input 508 (e.g., UID 116) for motion of the end effector 222. The user input may include unavailable movement, such as including unavailable rotation about an axis. The unavailable movement is projected, such as projecting rotation about one axis to rotations about just the two other axes. The projection may include other constraints, such as projection of the user input to one change in rotation due to DOF reduction and projection of the user input to another change in rotation due to a coupling between linear motion and rotation. The resulting projected user command is a function of both changes. The projection is provided for isolated movement to the unavailable and/or provided even when the movement is not isolated to the unavailable (e.g., user input is for translation along two axes and rotation about two axes where the robot arm 122 and surgical instrument 220 cannot rotation about one of the two axes when no other motion is provided).

The controller 502 is configured to solve for joint motion of the robotic arm and the surgical instrument with inverse kinematics from the projected user command. The solution is provided for part of or during medical teleoperation on a patient. The projected motion of the surgical instrument 220 is used to solve for joint commands to move the joints of the robot arm 122 and/or surgical instrument 220. These joint commands or motion are solved for in response to projection of user input of a move command. The user inputs a command to move (e.g., inputs a change or inputs a pose) the end effector 222 of the surgical instrument 220. The controller 502 is configured to project and then solve for the motion of the surgical instrument 220 through operation of the joints to provide the motion as projected.

The controller 502 is configured to solve for the motion with inverse kinematics. For example, a least square minimization of a difference between the motion of the surgical instrument 220 from the joint motions and the projected user command is used. Other optimizations relating the joint commands to the projections of end effector movement commands input by the user may be used.

The controller 502 is configured to control the robot arm 122 and surgical tool 220. Based on the solution from the inverse kinematics, one or more joints are moved in response to user inputs. The iterative inverse kinematic solution controls the joints.

The memory 504 or another memory is a non-transitory computer readable storage medium storing data representing instructions executable by the programmed controller 502. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for teleoperation of a surgical robotic system, the method comprising:
   receiving a user input to move a surgical tool coupled to a robotic arm, the user input having six degrees of freedom where the surgical tool has a lesser number of degrees of freedom;
   projecting the user input to the lesser number of degrees of freedom, the projecting including conversion of movement from a degree of freedom not of the lesser number to another degree of freedom of the lesser number;
   solving for joint motion of the robotic arm and surgical tool from the projected user input with inverse kinematics; and
   moving the robotic arm and/or surgical tool based on a solution from the solving.

2. The method of claim 1 wherein receiving comprises receiving the user input with rotation in three degrees of freedom where the surgical tool is rotatable in two degrees of freedom; and
   wherein projecting comprises projecting the user input from the rotation in the three degrees of freedom to rotation in the two degrees of freedom.

3. The method of claim 1 wherein receiving comprises receiving the user input from a handheld user interface device that is ungrounded, and wherein the user input is for an end effector of the surgical tool.

4. The method of claim 1 wherein projecting comprises maintaining the translation in three degrees of freedom and reducing the rotation from three degrees of freedom to the less than three degrees of freedom.

5. The method of claim 1 wherein receiving comprises receiving a first pose or first change in pose as the user input, and wherein projecting comprises converting the pose or change in pose to a second pose or second change in pose for which the surgical tool is capable.

6. The method of claim 1 wherein receiving and projecting occur in a command space for an end effector of the surgical tool prior to solving, and wherein solving comprises converting from the command space for the end effector to a joint space for joints of the surgical tool and robotic arm.

7. A method for teleoperation of a surgical robotic system, the method comprising:
   receiving a user input to move a surgical tool coupled to a robotic arm, the user input having six degrees of freedom where the surgical tool has a lesser number of degrees of freedom;
   projecting the user input to the lesser number of degrees of freedom;

solving for joint motion of the robotic arm and surgical tool from the projected user input with inverse kinematics; and moving the robotic arm and/or surgical tool based on a solution from the solving;

wherein projecting comprises projecting the user input for the rotation about first, second, and third axes as the three axes to rotation about just the first and second axes as the lesser number by a subtraction of a multiplication of (1) a dot product of a rotation about the third axis with a change in rotation of the end effector of the user input by (2) the rotation about the third axis.

8. The method of claim 7 wherein the user input is in a rotation matrix representation, and wherein projecting comprises converting the rotation matrix representation to an axis-angle representation, projecting in the axis-angle representation, and converting a result of the projecting back to the rotation matrix representation.

9. A method for teleoperation of a surgical robotic system, the method comprising:

receiving a user input to move a surgical tool coupled to a robotic arm, the user input having six degrees of freedom where the surgical tool has a lesser number of degrees of freedom;

projecting the user input to the lesser number of degrees of freedom;

solving for joint motion of the robotic arm and surgical tool from the projected user input with inverse kinematics; and moving the robotic arm and/or surgical tool based on a solution from the solving;

wherein projecting comprises projecting a change in rotation due to coupling between the translation and the rotation.

10. The method of claim 9 wherein projecting the change in the rotation due to the coupling comprises projecting with a similarity transform accounting for a remote-center-of-motion of the robotic arm.

11. The method of claim 9 wherein the projected user input is a function of the change in rotation due to the coupling and the projection to the lesser number of degrees of freedom.

12. The method of claim 11 wherein the function is a multiplication of the change in rotation due to the coupling, the projection to the lesser number, and the rotation about the three axes.

13. The method of claim 1 wherein solving comprises solving as a minimization of a least square.

14. A method for accounting for a limited degree of freedom of a tool in a surgical robotic system, the method comprising:

projecting a first pose from an ungrounded user interface with six degrees of freedom to a second pose of an end effector of a surgical tool held by a robotic arm where the second pose has only four or five degrees of freedom, wherein projecting comprises projecting with an axis-angle representation by a subtraction of a multiplication of (1) a dot product of a rotation about or translation on a first axis with a change in rotation or translation of the end effector by (2) the rotation about or translation on the first axis; and controlling the end effector based on the second pose.

15. A method for accounting for a limited degree of freedom of a tool in a surgical robotic system, the method comprising:

projecting a first pose from an ungrounded user interface with six degrees of freedom to a second pose of an end effector of a surgical tool held by a robotic arm where the second pose has only four or five degrees of freedom, wherein projecting comprises projecting with a change in rotation or translation due to a coupling between the rotation and translation about a first axis; and controlling the end effector based on the second pose.

16. The method of claim 14 further comprising receiving a user input command from a user interface, the first pose being of the end effector provided as the user input command.

17. The method of claim 14 wherein the second pose has only five degrees of freedom, a missing degree of freedom of the five degrees as compared to the six degrees being rotation about a first axis, and wherein projecting comprises maintaining three degrees of freedom in translation and projecting the rotation about the axis to rotation about second and third axes.

18. A surgical robotic system comprising:

a robotic arm;

a surgical instrument mountable to the robotic arm having an end effector where rotation about one axis is coupled to rotation about another axis;

a user interface device having three degrees of freedom in rotation; and a controller configured to project a user command from the user interface device for rotation about the one axis to rotations about the one axis and the other axis.

19. The surgical robotic system of claim 18 wherein the controller is configured to project the user command to a first change in rotation and to project the user command to a second change in rotation due to the coupling, the coupling being between linear motion and rotation, a projected user command being a function of the first and second changes, and the controller being configured to solve for joint motion of the robotic arm and the surgical instrument with inverse kinematics from the projected user command.

* * * * *